United States Patent [19]

Hirako

[11] Patent Number: 5,135,302
[45] Date of Patent: Aug. 4, 1992

[54] FLOW CYTOMETER

[75] Inventor: Shinichi Hirako, Nagaokakyo, Japan

[73] Assignee: Omron Corporation, Kyoto, Japan

[21] Appl. No.: 570,629

[22] Filed: Aug. 22, 1990

[30] Foreign Application Priority Data

May 15, 1990 [JP] Japan .............. 2-50686[U]

[51] Int. Cl.$^5$ .............................. G01N 21/53
[52] U.S. Cl. ........................ 356/73; 356/342; 356/339
[58] Field of Search ............ 356/73, 39, 343, 72, 356/336, 338, 339; 209/3.1, 579, 906

[56] References Cited

U.S. PATENT DOCUMENTS 4,318,481  3/1982  Lombardo et al. ............ 356/72
4,318,483  3/1982  Lombardo et al. ............ 356/72
4,790,653  12/1988 North, Jr. ...................... 356/39

Primary Examiner—Vincent P. McGraw
Assistant Examiner—LaCharles P. Keesee
Attorney, Agent, or Firm—Fish & Richardson

[57] ABSTRACT

This flow cytometer includes flow cell containing a flowing stream of a number of particles which flow one at a time in a straight line based on hydrodynamic methods, a radiator for radiating a light on the particles flowing through the flow cell, a forward scattered light detector for detecting a light scattered in the same direction as the radiating light, a right angle signal light detector for detecting light radiated in a right angle with respect to the direction of the radiating light, whereby the right angle signal light detecting assembly is disposed on a mount, with one end of the mount being elastically supported on a supporting member and the other end being disposed on another supporting member by an adjustment mechanism, whereby adjusting the inclination of the light axis of the right angle signal light detecting assembly is made easier so that the light axis can always be perpendicular to the radiated light.

8 Claims, 3 Drawing Sheets

FLOW CYTOMETER

FIELD OF INVENTION

This invention relates to a flow cytometer which analyzes a cell-like particle. More specifically, this invention relates to an adjustment mechanism for a light axis in such a flow cytometer.

REFERENCE TO RELATED APPLICATION

The subject matter of this application is related to the subject matter disclosed and claimed in commonly assigned application Ser. No. 07/570,631, filed Aug. 22, 1990.

BACKGROUND OF THE INVENTION

Conventional flow cytometers cause a number of particles such as cells to flow in a straight line in aqueous suspension. These particles are analyzed using a hydrodynamic method, whereby light is radiated onto particles flowing through a flow channel, thereby detecting the scattered light and fluorescent light from the particles and converting it to electronic signals for analysis. An important feature of the flow cytometer makes it possible to quickly analyze many particles at one time.

In FIGS. 3 and 4, such a conventional flow cytometer is shown.

Flow cell 10 has a flow channel 10a in which particles to be analyzed flow together with a sheath liquid. Each particle flows in a straight line in the flow channel 10a due to the hydrodynamic effect caused by the flow of sheath liquid. Focusing lens 7 focuses a beam Lo from a laser (not shown) onto particles flowing through the flow channel 10a.

Right angle light signal detecting assembly 21 is disposed in the y-axis plus direction and is perpendicular to the forward direction of beam Lo. The right angle signal light detecting assembly 21 contains light path tubes 22 and 23 and light path tube 22 is inserted into light path tube 23 in order to make the focusing adjustment as easy as possible. Light path tube 22 has collecting lenses 24 and 25 while tube 23 has pinhole 26 and light detector 27. The right angle signal L2 produced by a particle is collected by lenses 24 and 25, with its background noises eliminated by pinhole 26, is then received at light detector 27 where it is converted into electronic signals.

A forward scattering light detecting assembly 31 is disposed in the forward direction of the beam Lo (x-axis plus direction). The light detecting assembly 31 has light path tubes 32 and 35, (lens and pinhole not shown) and light detector 37, which receives scattered light L1 produced by particles and converts it into electronic signals. Beam blocker 33 prevents beam Lo from entering into light detector 37.

In the above-mentioned conventional flow cytometer, the light axis of right angle signal light detecting assembly 21 is required to be adjusted on the light radiating point A of flow channel 10a. In order to adjust the light axis with respect to the z-axis direction, it is well-known that light path tube 22 is provided with adjustment mechanism 20 for slideably adjusting in the z-axis direction and moving the end portion 22a of the light path tube slide in the z-axis direction by rotating adjustment screw 20a as shown in FIG. 3.

However, there are two problems with respect to the vertical movement caused by adjustment mechanism 20 as shown in FIG. 3. First, the mechanism 20 cannot slide end portion 22a smoothly. Second, after the adjustment of end portion 22a is completed, tightening the adjustment screw 20a to fix the position of end portion 22a causes a slight displacement of the adjusted position of end portion 22a thereby requiring a very expensive adjustment mechanism to avoid such displacement.

Further, if the entire right angle signal light detecting assembly is desired to be moved, a larger adjustment mechanism is required, thereby increasing the cost of the device and the complexity in its operation as well as making the smooth movement of adjustment more difficult.

SUMMARY OF THE INVENTION

In view of the above, it is an overall object of the present invention to provide a flow cytometer with a light axis which is easily adjustable by means of a simplified adjustment mechanism.

In order to achieve this object, the present invention is characterized in that the light axis of the right angle signal light detecting assembly is adjusted in parallel with the flow channel by adjusting the inclination within the plane which is perpendicular to the radiating light. Since the mount is elastically supported on the bench, its inclination is smoothly adjustable thereby enabling easier light axis adjustment. Moreover, the elastic supporting mechanism and adjustment mechanism are composed of a simple-like plate spring and screws respectively, so that it is possible to provide less expensive and simpler devices.

DETAILED DESCRIPTION OF THE INVENTION

Figure 1:
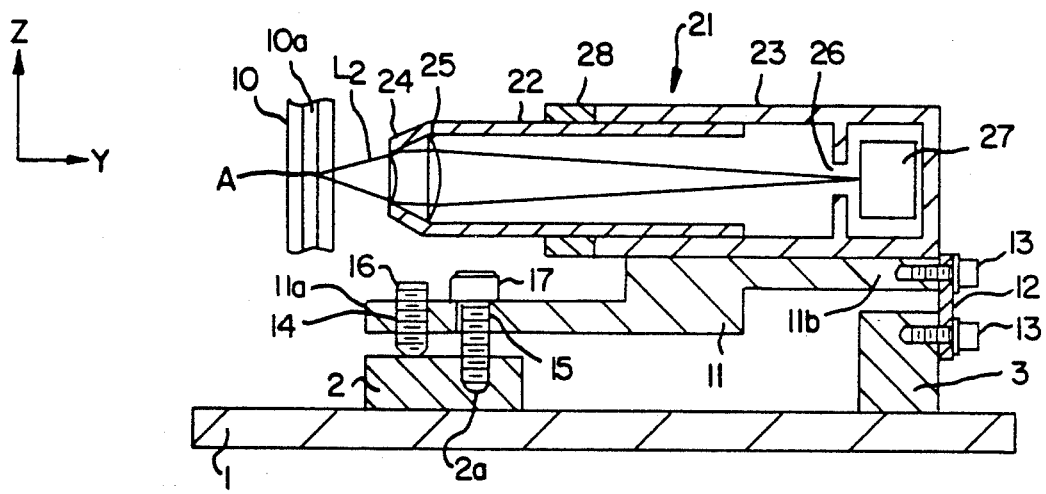
FIG. 1 is a cross-sectional view of a right angle signal light detecting assembly of a flow cytometer according to one of the embodiments of this invention.
Figure 3:
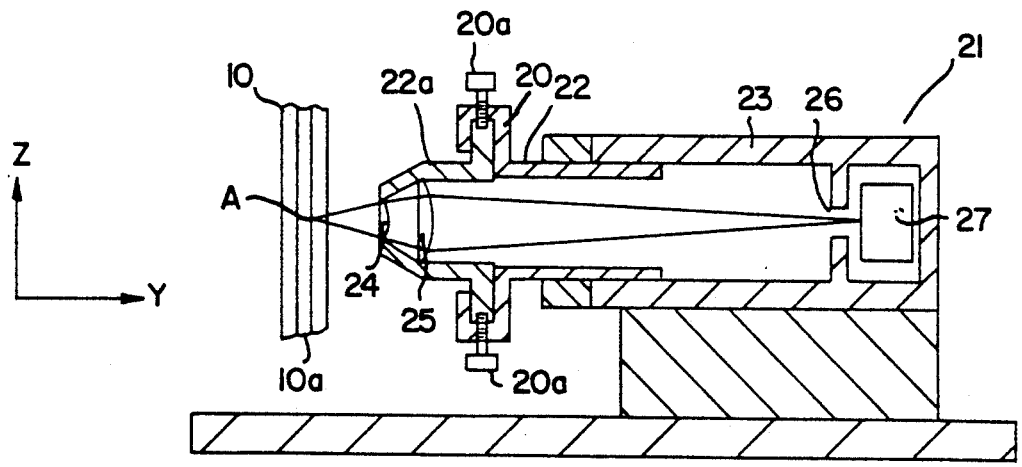
FIG. 3 is a cross-sectional view of a conventional right angle signal light detecting assembly.
Figure 2:
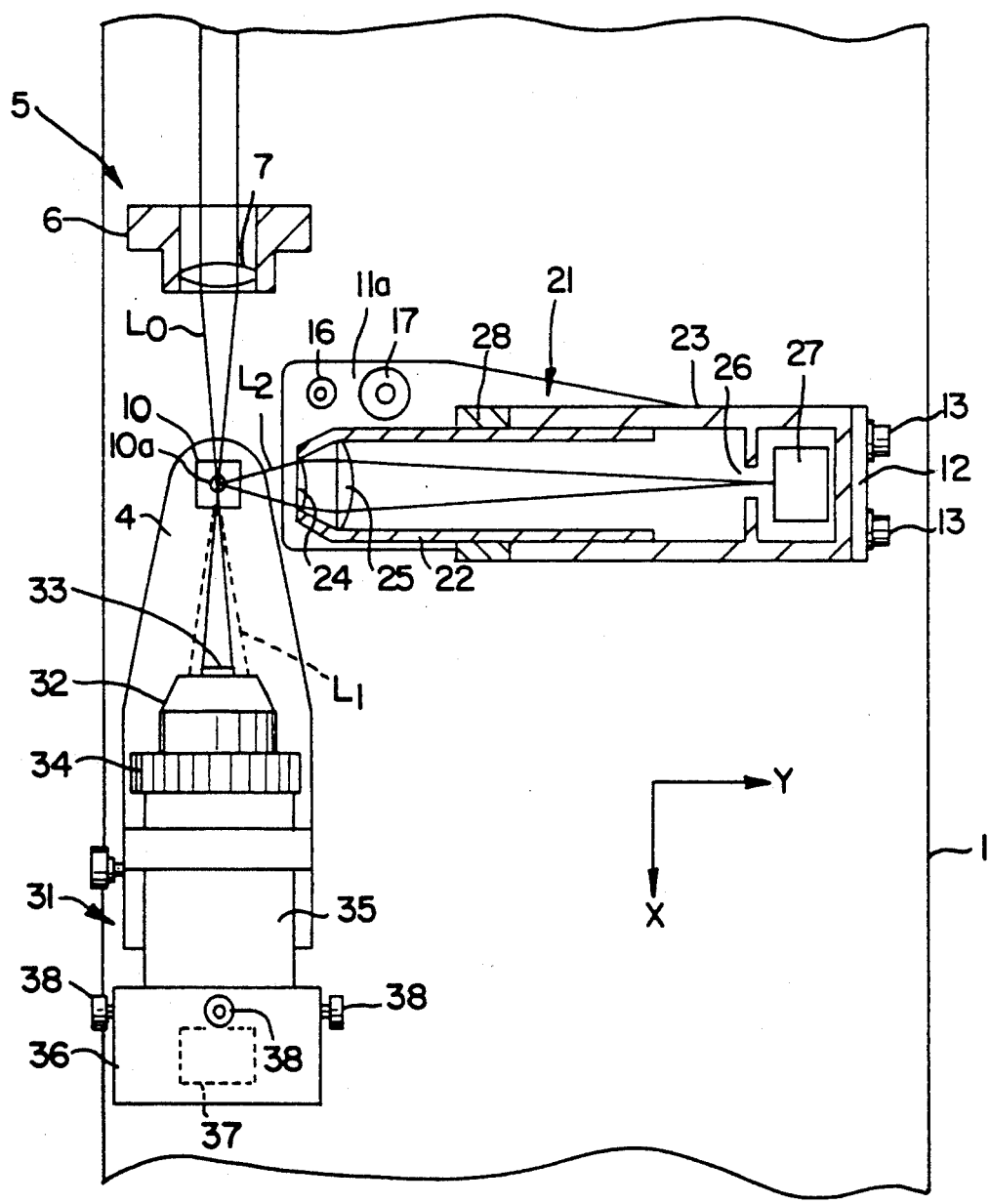
FIG. 2 is a plan view of the flow cytometer of this invention, a portion of which is a cross-section.
Figure 4:
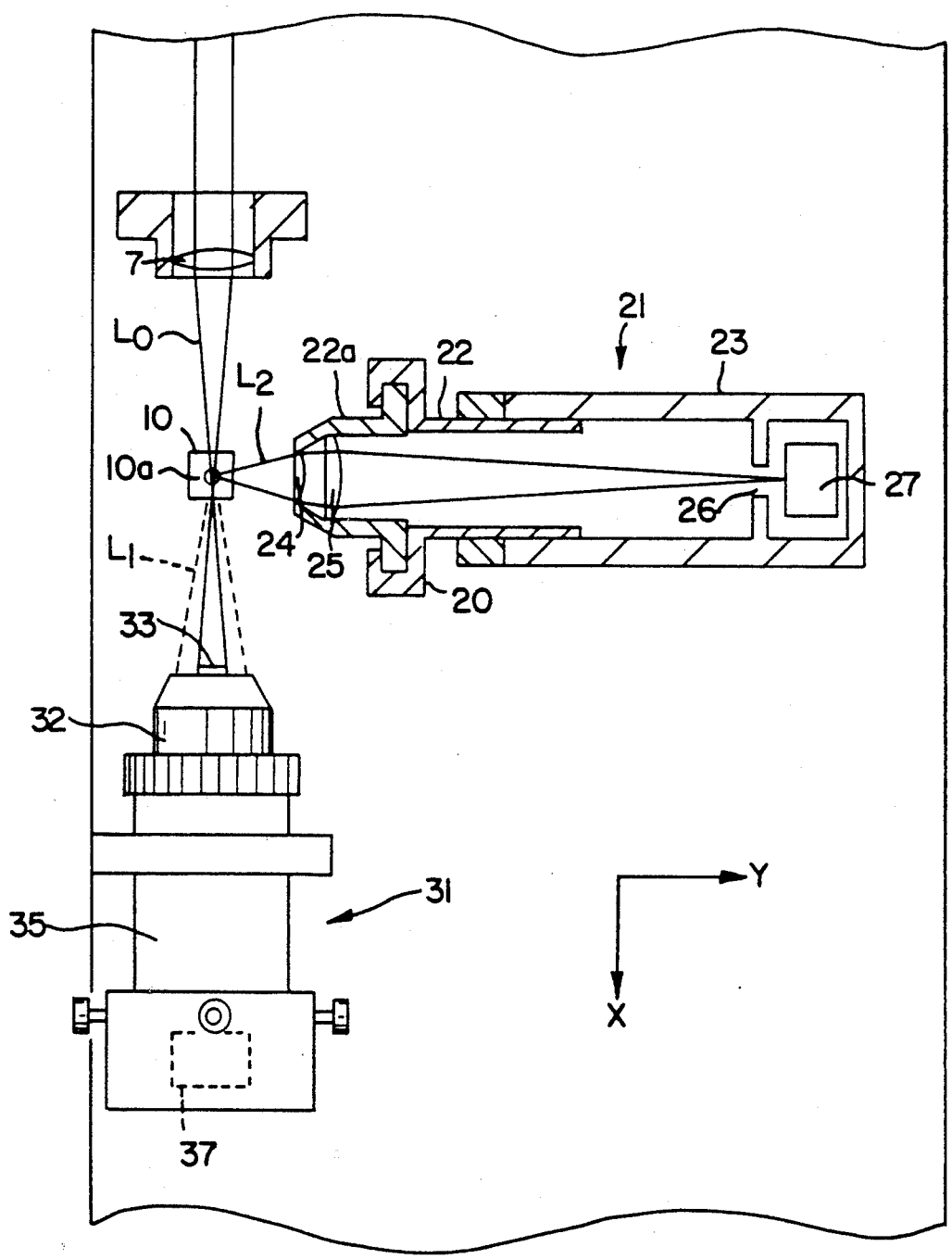
FIG. 4 is a plan view illustrating a flow cytometer employing the right angle signal light detecting assembly of FIG. 3.

One of the embodiments of this invention will be described by referring to FIGS. 1 and 2. A right angle signal light detecting assembly 21, forward scattering light detecting assembly 31, flow cell 10, among others, are disposed on flat bench 1. The right angle light detecting assembly 21 is fixed on mount 11, with front end 11a of mount 11 and rear end 11b each being supported by supporting members 2 and 3 respectively, such supporting members being fixed on bench 1.

Rear end 11b of mount 11 is supported through plate spring 12 on supporting member 3. The ends of plate spring 12 are fixed to rear end 11b of mount 11 and supporting member 3 respectively by screws 13.

The front end 11a of mount 11 has an extension on which vertical adjustment screw 16 and fixed screw 17 are disposed. The vertical adjustment screw 16 is engaged with nut 14 with nut 14 being disposed in front end portion 11a. The tip of screw 16 extends downward toward supporting member 2 and rests thereon. Alternatively, fixed screw 17 engages with nut 2a which is disposed in supporting member 2. The front end 11a of mount 11 is extended so that screws 16 and 17 are easily rotated from above.

Right angle light detecting assembly 21 has light path tubes 22 and 23. Light path tube 22 is inserted into light path tube 23 and has a pair of light collecting lenses 24 and 25 on its front end. Further, light path tube 23 has a pinhole 26 for eliminating background noise and light detector 27 for converting right angle signal light to electronic signals. The insertion depth of light path tube 22 into light path tube 23 is adjusted by rotating a focus ring 28. Flow cell 10 and forward scattered light detecting assembly 31 are both disposed on first mount 4 so as to be integrally mounted together. This mount 4 is disposed on bench 1. Mount 4 can be slightly adjusted in the x and y axis direction while the relative locational relationship between flow cell 10 and forward scattered light detecting assembly 31 is maintained. Accordingly, light axis adjustment of right angle signal light detecting assembly 21 within the x-y plane can be accomplished by moving flow cell 10 by means of mount 4.

Forward scattered light detecting assembly 31 has a light path tube 32 inserted into another light path tube 35. The insertion depth is adjustable by rotating focusing ring 34. Light path tube 32 has a beam blocker 33 and a collecting lens (not shown). A light path tube 35 is provided with a light detector container 36 wherein a light detector 37 and a pinhole (not shown) are accommodated. The locational relationship between light detector 37 and the pinhole is adjustable by screws 38 so that the forward scattered light L1 on the light axis of light detecting assembly 31 accurately reaches light detector 37.

Collecting lens assembly 5 includes a second mount 6 for mounting right angle signal light detecting assembly 21 and focusing lens 7 fixed thereon. Focusing lens 7 focuses a light beam Lo from a laser (not shown) and radiates the focused light beam Lo onto particles flowing through flow channel 10a.

Generally, a flow cytometer is provided with a processing unit for processing data signals from the pumping of the sheath liquid and samples and from light detectors 27 and 37; however, no description is provided because it is not a material part of this invention and because persons skilled in this art are familiar with such details.

The following is a description of the light axis adjustment of this flow cytometer. First, the light axis of forward scattered light detecting assembly 31 is adjusted to the center of flow channel 10a by using screws 38. Then, mount 4 is adjusted with respect to the y-axis direction, and the center of beam Lo is adjusted to be in line with the light axis of light detecting assembly 31. Further, mount 4 is adjusted with respect to the x-axis direction and the light axis of right angle signal light detecting assembly 21 is adjusted to be in line with the center of flow channel 10a within the x-y plane.

Further, the light axis of right angle signal light detector 21 is adjusted with respect to the z-axis direction. This adjustment is performed by varying the angle of the light axis of the right angle signal light detecting assembly 21 in the y-z plane which is completed by rotating vertical adjustment screw 16, after loosening fixed screw 17. The amount of protrusion under mount 11 of adjustment screw 16 is varied with the rotation of adjustment screw 16. Due to the weight of right angle signal light detecting assembly 21 and mount 11, the plate spring 12 bends causing the lower end portion of adjustment screw 16 to rest on top of supporting member 2. As the amount of protrusion of adjustment screw 16 varies, the height of the front end portion 11a of mount 11 also varies thereby enabling the adjustment of the inclination of the light axis in the z direction. At this moment, the rear end 11b of mount 11 is elastically supported by plate spring 12, thus ensuring smooth adjustment of the inclination.

After the completion of the adjustment, therefore, setting the light axis of beam focusing point A, the fixed screw 17 is tightened. Accordingly, the adjusted inclination of the right angle signal light detecting assembly 21 can be fixed without further movement of mount 11.

What is claimed is:

1. A flow cytometer comprising:
    a flow cell containing a flowing of a number of particles which flow one at a time in a straight line through a flow channel;
    a light radiating means for radiating light on the particles flowing through said flow cell;
    a forward scattered light detecting means for detecting light radiated in the same direction as said radiating light;
    a right angle signal light detecting means for detecting light radiated at a right angle with respect to the direction of said radiated light;
    a mount for said right angle signal light detecting means;
    an elastic support member provided at one end of said mount flexibly supporting one end of said right angle signal light detecting means on said mount;
    an adjustment mechanism at an opposite end of said mount from said elastic support member for smooth adjustment of the inclination of a light axis of the right angle signal light detecting means within a plane which is perpendicular to the direction of said radiating light.

2. A flow cytometer according to claim 1, wherein said forward scattering light detecting means comprises means for combining particles which are injected through a first inlet with a flowing stream of sheath liquid which is injected through a second inlet.

3. A flow cytometer according to claim 1, wherein said light radiating means comprises a laser device that radiates said light through a focusing lens whereby said focusing lens focuses said light onto the particles flowing in the flow channel.

4. A flow cytometer according to claim 1, wherein said forward scattered light detecting means comprises a forward scattered light detecting assembly which comprises a forward scattered light detector, light path tubes, a light collecting lens, a forward scattered light detector container, a forward focusing adjuster, a pinhole, adjustment screws, a beam blocker, said flow channel and said flow cell.

5. A flow cytometer according to claim 1, wherein said right angle light detecting means comprises a right angle light detecting assembly which comprises right angle light collecting lenses, right angle light path tubes, a right angle focusing adjuster, a right angle light collecting lens, a pinhole and a right angle light detector.

6. A flow cytometer according to claim 1, wherein said right angle light detecting means detects scattered light and fluorescent light.

7. A flow cytometer according to claim 1, wherein said light detected in said same direction as said radiating light is primarily scattered light.

8. A flow cytometer according to claim 1, wherein said flow cell is transparent with respect to any given wavelength and comprises synthetic quartz which is not fluorescent material.

* * * * *